(12) United States Patent
Schlemmer et al.

(10) Patent No.: US 7,199,875 B2
(45) Date of Patent: *Apr. 3, 2007

(54) FURNACE

(75) Inventors: Gerhard C. U. Schlemmer, Owingen (DE); Claus Busche, Huttenberg (DE)

(73) Assignee: Berthold GmbH & Co. KG (DE)

(*) Notice: Subject to any disclaimer, the term of this patent is extended or adjusted under 35 U.S.C. 154(b) by 0 days.

This patent is subject to a terminal disclaimer.

(21) Appl. No.: 11/100,181

(22) Filed: Apr. 6, 2005

(65) Prior Publication Data

US 2005/0190362 A1    Sep. 1, 2005

Related U.S. Application Data

(63) Continuation of application No. 10/167,788, filed on Jun. 12, 2002, now Pat. No. 6,894,776.

(30) Foreign Application Priority Data

Jun. 12, 2001 (DE) .................................. 101 28 272

(51) Int. Cl.
*G01N 21/74* (2006.01)

(52) U.S. Cl. ...................................... 356/312; 312/244

(58) Field of Classification Search ................ 356/312, 356/244
See application file for complete search history.

(56) References Cited

U.S. PATENT DOCUMENTS

| | | | |
|---|---|---|---|
| 4,953,977 A | 9/1990 | Tamm | 356/312 |
| 5,367,374 A | 11/1994 | Eichardt et al. | 356/312 |
| 5,408,316 A | 4/1995 | Eichardt et al. | 356/312 |
| 5,822,059 A | 10/1998 | Tobe et al. | 356/312 |
| 5,949,538 A | 9/1999 | Eichardt et al. | 356/312 |
| 5,981,912 A | 11/1999 | Gilmultdinov et al. | 219/398 |
| 6,020,958 A | 2/2000 | Tobe et al. | 356/312 |
| 6,545,757 B1 | 4/2003 | Eichardt et al. | 356/312 |
| 6,552,786 B1 | 4/2003 | Frech et al. | 356/312 |

*Primary Examiner*—Layla G. Lauchman
(74) *Attorney, Agent, or Firm*—St. Onge Steward Johnston & Reens LLC

(57) ABSTRACT

A furnace, in particular for an electro thermal atomization device of an atom absorption spectrometer, has a heatable heat duct in which is mounted a trial platform. The trial platform is essentially basin-shaped with radially inward-turned rims, at least at its free ends. In order to make ongoing improvements in a furnace of the aforementioned type, so that the trial platform has an increased lifetime along with high reproducibility of measurements and simple operation as well as low cost, the trial platform features a geometric structure stabilization device which reduces the ratio of effective volume of the trial platform to the rim volume.

18 Claims, 2 Drawing Sheets

FURNACE

Figure 1:
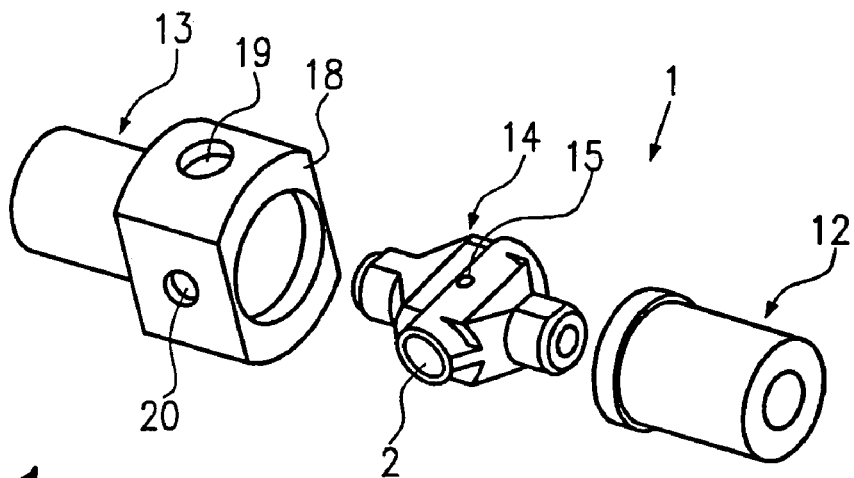
Figure 2:
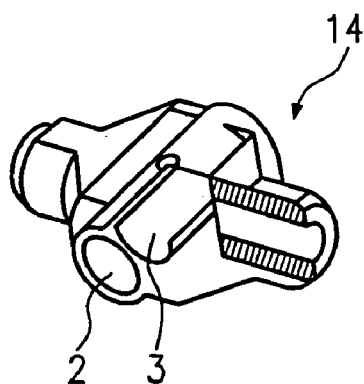

This is a continuation of copending U.S. patent application Ser. No. 10/167,788 filed on Jun. 12, 2002 now U.S. Pat. No. 6,894,776, which claims priority of German Patent Application 10128272.9 filed on Jun. 12, 2001.

FIELD OF THE INVENTION

The invention relates to a furnace, in particular for an electro thermal atomization device of an atom absorption spectrometer, with a heatable heat duct in which is mounted a trial platform, which is essentially basin-shaped with radially inward-turned rims, at least at its free ends.

BACKGROUND OF THE INVENTION

A trial atomization is performed on the trial platform. After the appropriate supply of heat within the heat duct, through the irradiation of electromagnetic waves of determined frequency into the heat duct these waves are absorbed by the atomized trial and a resulting absorption spectrum is registered, which is characteristic for the respective trial. The corresponding absorption spectrum is determined by the atom absorption spectrometer.

The trial platform has a certain effective volume, into which the corresponding trial can be inserted by means of a pipette or the like. At its free ends, the basically basin-shaped trial platform is generally equipped with partially circular rims, which restrict the effective volume in a lateral direction.

Trial platforms in common use heretofore have proved, at relatively high temperatures and especially under the impact of strongly oxidizing reagents, to lose their shape and to give way against an inside wall of the heat duct. This increases the contact surface between the trial platform and the heat duct, resulting in such a strong heating of the trial platform by the introduction of heat from the heat duct that there is no longer an optimal temperature delay relative to the heat duct. Such a temperature delay, however, is desirable in order to improve and stabilize the atomization conditions for the elements to be determined, also in respect to continuing high increments of heat at high temperature.

It should also be mentioned that, even with a minor loss of shape of the trial platform, the measurements are no longer reproducible. For all these reasons the trial platform must be replaced if there is a corresponding loss of shape. This is relatively difficult and, in some cases, in addition to the trial platform the heat duct at least must also be replaced, resulting in increased costs.

The invention therefore aims to make ongoing improvements in a furnace of the aforementioned type, so that the trial platform has an increased lifetime along with high reproducibility of measurements and simple operation as well as low costs.

According to a preferred embodiment of the invention, this task is fulfilled in that the trial platform has a geometric structure stabilization device, which reduces the ratio of the effective volume of the trial platform to the rim volume. In the invention disclosure, the rim volume refers to a volume occupied by the rims of the trial platform.

The structure stabilization device prevents the trial platform from prematurely losing its shape and keeps the contact surfaces between the trial platform and the heat duct from increasing. As a result, on the one hand, the lifetime of the trial platform is increased. An increased lifetime also leads to a cost reduction in operating the furnace. In addition, the stabilized structure of the trial platform results in a good reproducibility of the measurements carried out with the trial platform. Another result of the stabilized structure is that even aggressive media can be injected into it better and with increased lifetime of the trial platform and can be measured by means of an atomic absorption spectrometer.

It is true that the effective volume of the trial platform is to some extent reduced by the structure stabilization device. This reduction, however, is relatively slight, so that sufficient trial material can be injected even with the inventive trial platform. In addition, the trial platform of this invention can be larger than a known trial platform while retaining the same amount of space in the heat duct, and thus the effective volumes of the inventive trial platform and of the known trial platform are essentially equal.

The inventive trial platform can be used particularly in a heated graphite atomizer (HGA). This is also true for transversally heated graphite atomizers (THGA).

To ensure that the trial platform is easy to operate and that it can fit in the heat duct, it can be integrated into the heat duct. The integration is normally ensured by means of a basically punctiform connection with the heat duct. In the remaining area no direct contact should exist between the trial platform and the heat duct, in order to minimize any heating through the addition of heat between the tube and the platform.

Such an integrated trial platform is generally of small mass and has a relatively large surface. In the case of one trial platform in common use, its length for example is 10 mm, the thickness of the rim is 0.47 mm, and the corresponding height of the rim is 0.08 mm. Because of the small mass and the great surface, the trial platform can be heated up quickly by heat rays emitted from the heat duct. The punctiform connection with the heat duct results in an optimal temperature delay with respect to the tube, a very desirable characteristic for a trial platform with stabilized temperature.

A trial platform that can be produced simply and relatively economically, which contains little uncleanliness, and which is relatively easy to operate can be formed of graphite as its base material. A surface coating is generally applied to this base material pyrolytically. The surface coating increases the chemical stability of the platform.

In order to maintain the known advantages of existing trial platforms in the inventive trial platform without having to use other materials, additional materials, additional structural elements or the like, the invention proposes the geometrical structure stabilization device. This installation can, for instance, be configured through a reduction of the platform length. The corresponding length reduction in comparison to the existing trial platforms results, in simple manner, in a stabilization of the trial platform, considerably prolonging its effective life; that is, the shape of the trial platform is stable for a longer period.

Such a length reduction and other minor modifications in the geometry of the trial platform can lead to a smaller effective volume. This is tolerable, however, since the effective volume of the inventive trial platform remains well suited for receiving a sufficient trial quantity for carrying out corresponding measurements.

It was observed that the platform length could be reduced by 10 to 40 percent in comparison to known platforms while maintaining a sufficiently large effective volume. It is considered advantageous to have a reduction between 15 and 35 percent, and especially favorable if it is in the range of 20 to 30 percent. A 30 percent reduction in length will result, for instance, from a decrease in platform length from 10 mm to 7 mm.

Another means of forming the structure stabilization device, while maintaining the length of the trial platform, is by increasing the rim thickness of the platform. Otherwise the other geometric dimensions of the trial platform can be maintained unchanged in comparison to a known trial platform.

Even a great rim thickness results in a low decrease in the effective volume which in no way affects the use of the trial platform for conducting corresponding measurements.

It was observed that increases in the rim thickness ranging from 10 to 50 percent in comparison to known platforms are sufficient. A thickening of 25 to 45 percent is preferable, and a thickening of 30 to 40 percent is particularly advantageous. An increase in rim thickness of 0.65 mm produces a thickening of the rim by about 38 percent, for instance, in comparison to a rim thickness of 0.47 mm in a known trial platform.

An additional means of configuring the geometric structure stabilization device is through an increase in the height of the rim. Once again the other geometric dimensions of the trial platform can remain unchanged in comparison to known trial platforms. In increasing the height of the rim, care must be taken that it is not so great as to influence the irradiated electromagnetic waves that are to be absorbed by the atomized trial. This can occur, for instance, through a more precise arrangement of the heat duct and/or trial platform relative to the direction of radiation of the electromagnetic waves.

It has been shown that it is possible to increase the rim height of the trial platform by 40 to 240 percent in comparison to known trial platforms. An increase of 80 to 200 percent is preferable, and of 100 to 150 percent is particularly advantageous. For instance, a 125 percent increase of rim height has been achieved with a rim height of 0.18 mm as opposed to a rim height of 0.08 mm in a trial platform that is in common use.

In relation to the aforementioned concrete values, it should be pointed out that they are provided only by way of example. A corresponding geometric structure stabilization device can also be used in trial platforms in current use, which have other concrete values for length, rim thickness, and rim height.

In order to stabilize the inventive structure still further, the geometric structure stabilization device can simultaneously include a reduction of the platform length and/or an increase of the rim thickness and/or an increase of the rim height.

Since the trial platform as a rule always includes a certain pretensioning, there can be an additional advantageous impact on this pretensioning if an increase in rim thickness and/or in the rim height is arranged, for instance, at just one end of the platform. In this respect, it is important to remember that it is possible, for instance, that an increase in rim thickness could occur at one end of he platform and an increase in rim height at the other end, or vice versa.

It is possible, in addition, that an increase in both rim thickness and rim height could occur at one end, whereas at the other end of the platform there is only an increase in rim height or in rim thickness. Other combinations of corresponding geometric structure stabilization devices are obvious.

BRIEF DESCRIPTION OF DRAWINGS

In the following discussion, advantageous embodiments of the invention will be examined in greater detail with the help of the associated illustrations. The illustrations are as follows.

FIG. 1 A perspective top view of an exploded furnace with heat duct.

FIG. 2 A partially cut-out detailed view of an element of FIG. 1.

FIG. 3 An initial model of a trial platform in the heat duct according to FIG. 2, in a partially cut-out view.

FIG. 4 A second model of a trial platform in a view comparable to that of FIG. 3.

FIG. 5 A third model of a trial platform in a view comparable to that of FIG. 3.

DETAILED DESCRIPTION OF DRAWINGS

FIG. 1 depicts an inventive furnace 1 consisting of three furnace parts 12, 13, and 14, in a perspective top view. The middle oven part 14 contains a heat duct 2 in which, as seen in FIG. 2, a trial platform 3 is integrated. A trial can be conducted to this platform by way of a trial opening 15 on an upper side of the middle oven part 14 by means of a pipette or the like.

The heat duct 2 includes two cylindrical extensions of medium caliber, to which a right or left furnace part 12, 13 can be attached. In particular, the heat duct 2 is warmed by means of the bored holes.

The left furnace part 13 has a housing 18 into which the middle furnace part 14 can be installed. If this middle furnace part is attached in the housing 18, the trial opening 15 is aligned with the opening 19 and the ends of the heat duct 2 are aligned with the openings 20 in the housing 18.

FIG. 2 shows the middle furnace part 14 in isolated position and partly cut out. In particular, the arrangement of the trial platform 3 can be recognized inside the heat duct 2.

FIG. 3 presents an initial model of a trial platform 3 with a geometric structure stabilization device 8. The corresponding heat duct 2 is partly cut away and in the interior of the heat duct the basically basin-shaped trial platform 3 is approximately centered on the longitudinal axis of the heat duct 2. The trial platform has a rim 6, 7 on its ends 4, 5. This rim has the shape of a circle segment and stands radially inward from the trial platform 3.

In the model shown in FIG. 3, the geometric structure stabilization device 8 is formed by an increase of at least rim thickness 10 of the rim 5. On the other hand, the rim 6 has an unchanged rim thickness 16. An effective volume of the trial platform 3 is formed between the rims 6, 7 and by the corresponding rim height. This effective volume can be filled by way of the trial opening with a corresponding trial.

The rim 6 can also be formed with an increased rim thickness 10 corresponding to rim 5. In this case the geometric structure stabilization device 8 would be formed by the increased rim thickness 10 of both rims 6, 7.

FIG. 4 depicts a second model for a trial platform 3. This embodiment is distinguished from the one in FIG. 3 by the fact that the rim 7 on the end 5 of the trial platform 3 has an increased rim height 11 in comparison with the rim height of rim 6. Analogously to FIG. 3, this increased rim height 11 can also be provided for rim 6 at the other end 4 of the trial platform 3.

In the model in FIG. 4, the geometric structure stabilization device 8 is formed by the increased rim height 11.

In connection with the model according to FIGS. 3 and 4, it should be mentioned that a platform length 9 as in FIG. 5 is unchanged and is equal in both models. In addition, the models in FIGS. 3 and 4 can be combined, since for instance rim 7 has both the increased rim thickness 10 and the increased rim height 11. Finally, it is also possible that, for instance in the model of FIG. 4, the rim 6 on the end 4 of the trial platform 3 is provided with an increased rim thickness 10 as in FIG. 3, or the rim 6 of FIG. 3 is equipped with an increased rim height 11 as in FIG. 4.

Figure 3:
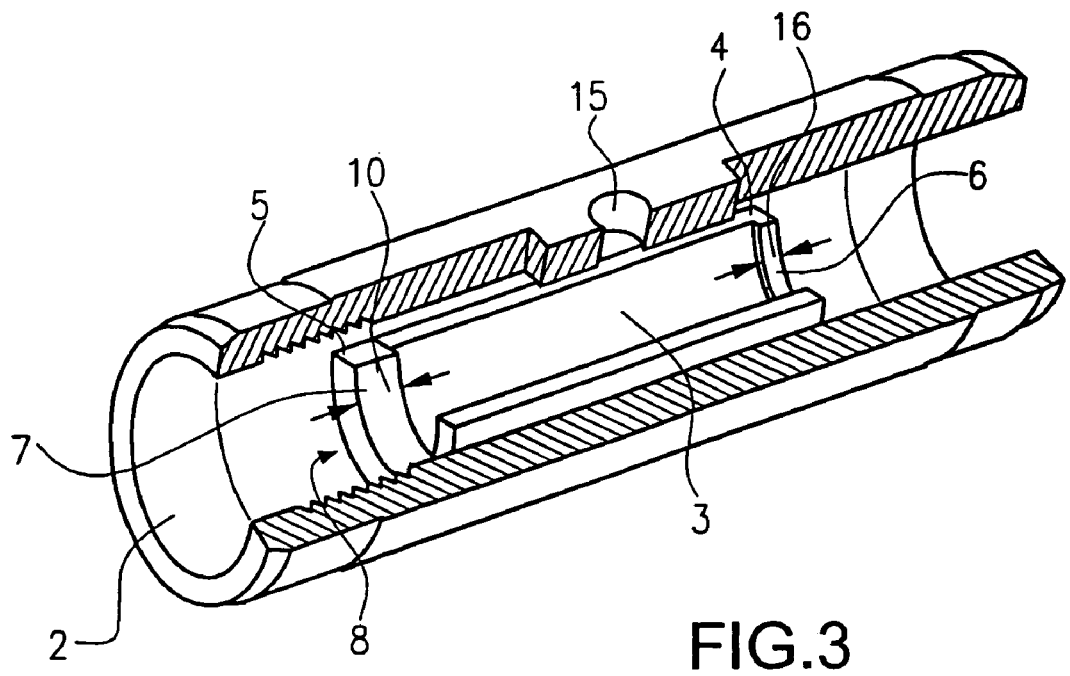

A third model of a trial platform is shown in FIG. 3. This model is differentiated from the preceding models by the fact that the platform length 9 is reduced in comparison to the platform length 17 while maintaining the thickness and heights of the rims 6, 7. The corresponding geometric structure stabilization device 8 is formed by this reduction of the platform length 9.

Figure 4:
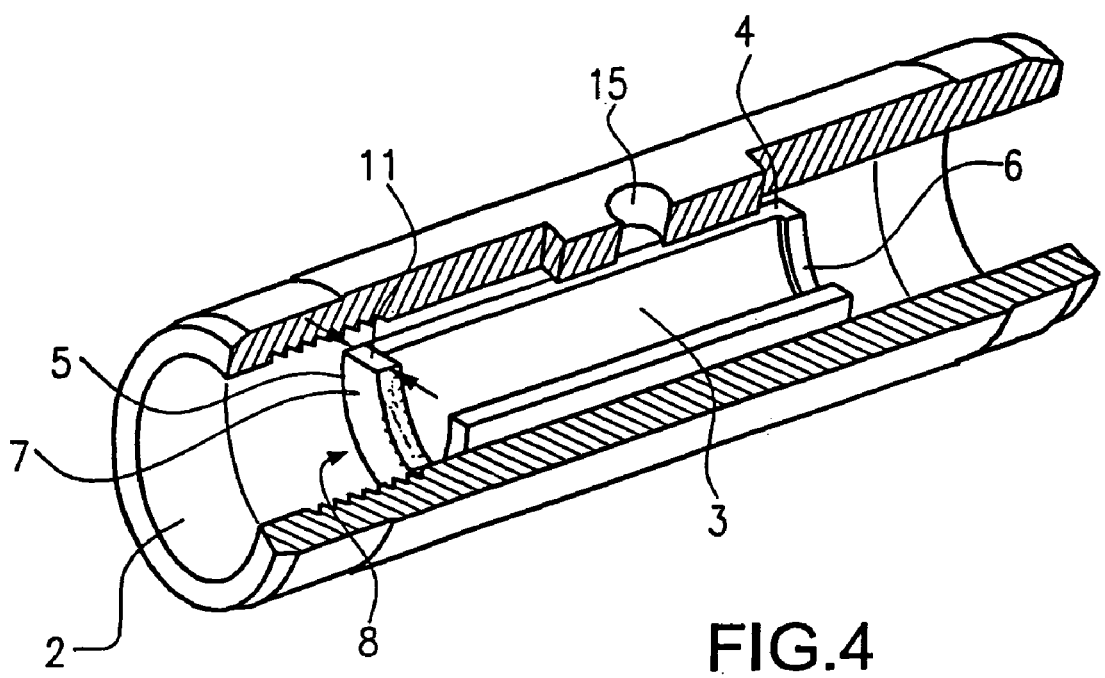
Figure 5:
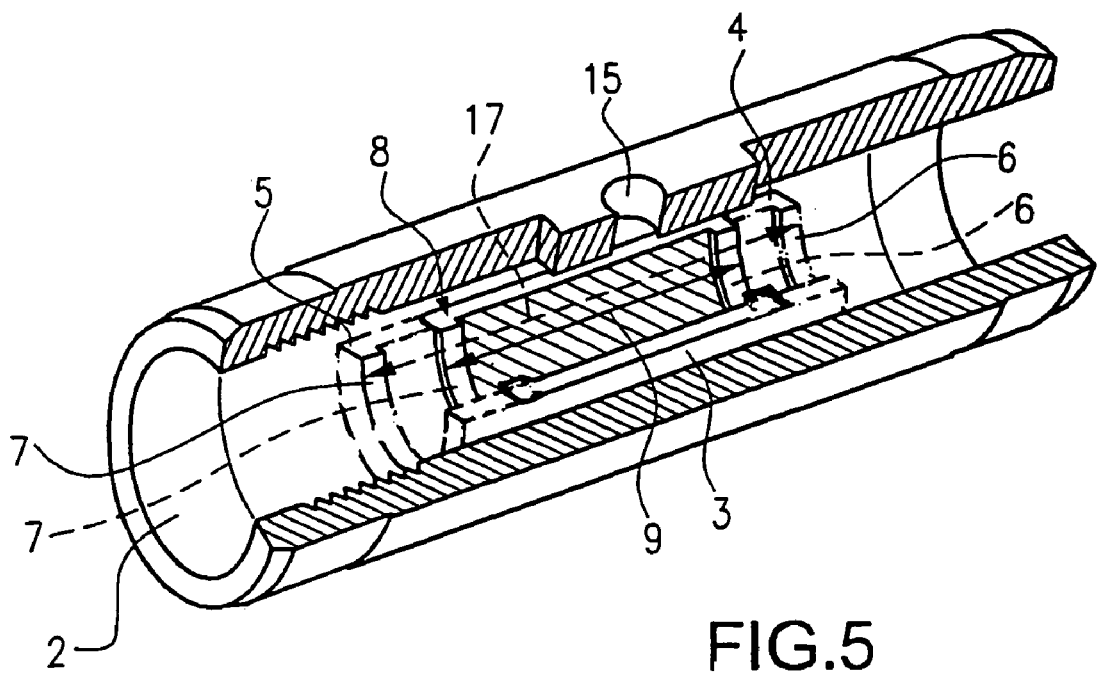

It should be mentioned that also in this connection it is possible to combine the various models of FIGS. 3 to 5. An example of such a combination occurs if the trial platform 3, with reduced platform length 9 for instance, has an increased rim thickness 10 and/or an increased rim height 11 on one or both rims 6, 7. Analogously, in the models of FIGS. 3 and 4 as well, the platform length can be reduced to correspond to FIG. 5.

As a result of the invention, through a simple geometric structure stabilization device a trial platform of a heat duct is further improved in its ability to retain its shape by the fact that the lifetime of the trial platform is considerably increased; that is, a contact between trial platform and heat duct is reduced to the essentially punctiform connection between them, while otherwise the trial platform and heat duct are arranged at a distance from one another. Thanks to this improved shape retention of the trial platform, remarkable advantages can be achieved with simple means while retaining all advantages of known trial platforms in current use. In addition to the increased stable shape in itself, there is also a long-term stability even at high temperatures inside the furnace. The reproducibility of measurements conducted by the inventive trial platforms is extremely high and is also ensured over a lengthy period of time.

At the same time, the proposed geometric structure stabilization devices in no way influence the structure of the trial platform or the materials used for the trial platform, since no additional structural elements or additional materials need to be used.

The invention claimed is:

1. A furnace for an electro thermal atomization device of an atom absorption spectrometer, comprising:
a heat duct for supplying heat within the heat duct; and
a trial platform mounted within the heat duct, the trial platform having a platform length and being essentially basin-shaped with radially inward-turned rims, at least at its free ends, each of the rims having a rim thickness and a rim height, the platform length, the rim thickness and the rim height of the trial platform being selected in a manner such that the ratio of effective volume of the trial platform to a rim volume occupied by the rims of the trial platform is reduced.

2. The furnace in accordance with claim 1, wherein the furnace is a heated graphite atomizer that is transversally heatable.

3. The furnace in accordance with claim 1, wherein the trial platform is integrated in the heat duct.

4. The furnace in accordance with claim 3, wherein the trial platform is formed of graphite as base material, on which an overcoating is applied pyrolytically.

5. The furnace in accordance with claim 1, wherein the ratio of effective volume of the trial platform to the rim volume is reduced by a reduction of the platform length.

6. The furnace in accordance with claim 5, wherein the reduction of the platform length is in the range from 10 to 40 percent.

7. The furnace in accordance with claim 5, wherein the reduction of the platform length is in the range from 15 to 35 percent.

8. The furnace in accordance with claim 5, wherein the reduction of the platform length is in the range from 20 to 35 percent.

9. The furnace in accordance with claim 1, wherein the ratio of effective volume of the trial platform to the rim volume is reduced by an increase in the rim thickness.

10. The furnace in accordance with claim 9, wherein the increase in rim thickness is in the range between 10 and 50 percent.

11. The furnace in accordance with claim 9, wherein the increase in rim thickness is in the range between 25 and 45 percent.

12. The furnace in accordance with claim 9, wherein the increase in rim thickness is in the range between 30 and 40 percent.

13. The furnace in accordance with claim 1, wherein the ratio of effective volume of the trial platform to the rim volume is reduced by an increase in the rim height of the trial platform.

14. The furnace in accordance with claim 13, wherein the increase in the rim height is in the range between 40 and 250 percent.

15. The furnace in accordance with claim 13, wherein the increase in rim height is in the range between 80 and 200 percent.

16. The furnace in accordance with claim 13, wherein the increase in rim height is in the range between 100 and 150 percent.

17. The furnace in accordance with claim 1, wherein the ratio of effective volume of the trial platform to the rim volume is reduced simultaneously by a reduction of the platform length and/or an increase in the rim thickness and/or an increase in the rim height.

18. The furnace in accordance with claim 17, wherein the increase in the rim thickness and/or the increase in the rim height is found at least on one end of the trial platform.

* * * * *